United States Patent [19]

Kratzer et al.

[11] Patent Number: 4,604,894
[45] Date of Patent: Aug. 12, 1986

[54] SYSTEM FOR MEASURING BLEEDING TIME IN VITRO

[76] Inventors: Michael Kratzer, Leopoldstr. 56, D-8000 München 40, Fed. Rep. of Germany; Gustav V. R. Born, 10 Woodland Gardens, Muswell Hill, London N10 3UA, England

[21] Appl. No.: 563,454
[22] Filed: Dec. 20, 1983

[30] Foreign Application Priority Data

Dec. 23, 1982 [DE] Fed. Rep. of Germany ....... 3247815

[51] Int. Cl.⁴ .................. G01N 11/04; G01N 33/48
[52] U.S. Cl. ........................... 73/64.1; 422/73; 436/69
[58] Field of Search ............... 73/64.1; 422/73; 436/69

[56] References Cited

U.S. PATENT DOCUMENTS

| | | | |
|---|---|---|---|
| 3,486,859 | 12/1969 | Greiner et al. | 73/64.1 X |
| 3,890,098 | 6/1975 | Moreno | 73/64.1 |
| 3,911,728 | 10/1975 | Fixot | 73/64.1 X |
| 3,918,908 | 11/1975 | Moyer et al. | 73/64.1 X |
| 4,000,972 | 1/1977 | Braun et al. | 73/64.1 X |
| 4,074,971 | 2/1978 | Braun et al. | 73/64.1 X |
| 4,454,752 | 6/1984 | Scordato | 73/64.1 |

*Primary Examiner*—Jerry W. Myracle
*Assistant Examiner*—Joseph W. Roskos
*Attorney, Agent, or Firm*—Fleit, Jacobson, Cohn & Price

[57] ABSTRACT

A system for measuring bleeding time in vitro is disclosed in which blood is passed under pressure through a porous element and the resulting volumetric flow is measured. The porous element is provided with a through aperture and supported in such a manner that the blood moves through the aperture and not laterally into the porous element. The porous element can be soaked in a solution, for example, adenosine diphosphate, which coagulates the platelets and in this manner it is possible to reproduce in vivo bleeding conditions.

18 Claims, 3 Drawing Figures

U.S. Patent      Aug. 12, 1986      4,604,894
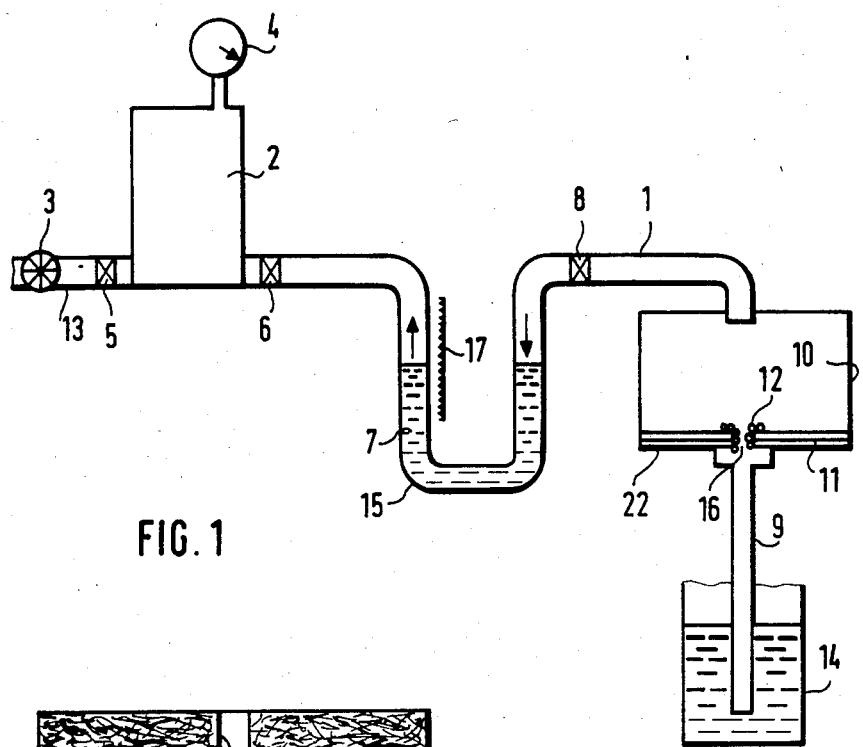
FIG. 1
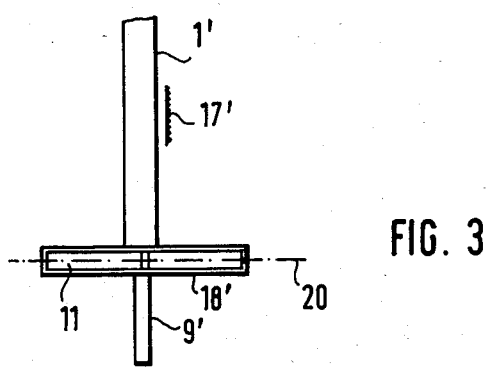
FIG. 2
FIG. 3

SYSTEM FOR MEASURING BLEEDING TIME IN VITRO

The present invention relates to a system that is used for measuring bleeding time in vitro.

In the blood platelet coagulometer according to G. V. R. Born, platelet-rich plasma is kept in convectional motion by means of a stirrer, which is done in a conventional manner. Platelet coagulation is initiated by a defined stimulus, for example, the addition of adenosine phosphate. At the same time, a photocell is used to measure light transmission. If the blood cells coagulate, light transmission increases. The amplitude and the speed of the increase in the photocurrent provide a measure of the tendency of the blood platelets to coagulate.

In a further procedure for determining in vitro bleeding time, described by Didisheim, native or anticoagulated blood is pumped through a plastic hose, in the side of which there is a hole having a diameter of approximately 200 microns. After some 5 minutes, the hole becomes plugged by the blood that flows through it. Thus, the bleeding time established by this instrument is dependent, among other factors, on the tendency of the platelets to coagulate.

British Pat. No. 2,096,329 describes a process and a system which makes the coagulation tendency of thrombocytes suspended in the blood amenable to measurement. When this is done, a blood sample is kept at a constant temperature in a container. The end of a tube is immersed in the container, and the other end of the tube is connected through a valve to a source that generates a constant vacuum. When the valve is opened, the blood is drawn through the submerged end of the tube. At one end, the diameter of the tube is such that the aperture becomes clogged by the coagulation of the thrombocytes suspended in the blood. The volumetric flow of the blood through the aperture, which takes place at a constant pressure drop, is determined by a metering system. In this way, it is possible to simulate the bleeding process in vivo.

It is an object of the present invention to provide a system of the type described above which both significantly reduces the susceptibility of failure of the measurement procedure which results from the microthrombs in the blood and also permits a significant increase in reproducibility.

These objects are achieved by providing a system for measuring bleeding time in vitro. The system is characterized by the features described in claim 1.

An important advantage of the present invention is that the essential aspect of the procedure that is carried out is based on the in vivo situation found in bleeding (from a minor artery).

According to a configuration of the present invention, the porous material of the element is soaked in a solution that coagulates the platelets, for example, a solution of adenosine diphosphate. By this means, it is possible to reproduce more precise bleeding conditions under in vivo conditions since, in an actual trauma, adenosine phosphate is secreted from the walls of the blood vessel and this induces coagulation of the platelets.

The invention can be further characterized by incorporating a capillary ahead of or after the aperture, and in this matter it becomes possible to simulate the resistance of a small artery from which the bleeding is taking place and to reproduce hemodynamic conditions under in vivo conditions.

The tendency of the platelets to coagulate, which determines the bleeding time, is a parameter that is very frequently used for clinical diagnosis and assessment of the medical effectiveness of anticoagulation substances. Substances of this kind are administered, for example, in cases of coronary infarction or arterial blockage. The present invention renders such diagnoses or assessments simple, rapid and reproducible for the first time, without excessive personnel requirements.

The invention will now be described in greater detail with reference to the acoompanying drawings, in which:

FIG. 1 is a schematic diagram of a system for measuring bleeding time in vitro;

FIG. 2 is a large scale illustration of the portion that consists of porous material and incorporates the aperture; and FIG. 3 is a fragmentary schematic view of a simplified version of the invention.

In FIG. 1, a chamber 10 accommodates an element 11 made of porous material, the element 11 having an aperture 16. A tube 1 is connected securely to the chamber 10 and contains valves 6 and 8, and ends in a reservoir 2 that is under negative pressure. This vacuum is generated in the reservoir 2 by means of a pump 3, the pump being connected to the reservoir by the line 13 and the valve 5. A metering system 4 is installed on the reservoir 2, and this meeting system indicates the negative pressure that is effective in the reservoir 2.

The blood that is to be drawn through a capillary tubing 9 through the aperture 16 of the element 11 which is of porous material is held in a container 14, which can be, for example, a plastic bowl, that, as is described in United Kingdom Pat. No. 2,096,329, can be arranged in a metal container in which there is water that is maintained at a temperature of 37 deg. C.

In order to ensure that no air is drawn through the porous material, the element 11 preferably rests on a base 22, which has an opening in the area of the aperture 16. The base 22 is connected tightly to the chamber 10 and the capillary 9. As an example, the base 22 can consist of a panel on which there is a layer of rubber that is located between the panel and the porous material. In addition, the base ensures that no blood flows along the outer surfaces from one side of the element 11 to the other side of the element 11. This can also be ensured, for example, by sandwiching the element 11 between two panels which have openings in the area of the aperture 16 and which are connected tightly to capillary tubing 9, or tubing 9' and tube 1' (described later with reference to FIG. 2).

It is preferred that there be a U-bend in the tube 1, in the interior of which there is a coloured liquid 7. When blood is drawn through the aperture 16 in the element 11 as a result of the valves 6 and 8 being opened, the coloured liquid 7 within the U-bend 15 will be displaced in the direction indicated by the arrow. The displacement of the coloured liquid 7 thus becomes a measure of the volumetric flow of blood that occurs through the aperture 16. This displacement of the level of the coloured liquid in one side of the U-bend 15 can be determined by means of the schematically represented measuring device 17. It is preferred that this measuring device be an electro-optical measuring system of the type described in United Kingdom Pat. No. 2,096,329 (FIG. 2), which indicates the changes in the volumetric flow of the blood through the aperture 16 as a function of time.

In place of the tube 1 with the U-bend 15, the displacement of a coloured liquid within a straight tube that is arranged horizontally can be used to determine the volumetric flow through the aperture 16. A measuring system of this kind is also described in United Kingdom Pat. No. 2,096,329 (FIG. 3).

In addition, it is also possible to measure the pressure differential that exists between locations ahead of and after the aperture. This measurement constitutes an indication of the degree of closure of the aperture, i.e., of the coagulation of the blood in the vicinity of the aperture.

The porous material of the element 11 is such that the blood particles cannot be drawn through the material. This ensures that the blood particles actually pass through the aperture only and do not enter the edge areas of the aperture 16.

The element 11 that is of porous material consists preferably of a filter material in which a single hole, which constitutes the aperture 16, is stamped. FIG. 2 shows the part 11 at an enlarged scale.

It is preferred that the size of the pores in the filter material be less than 5 microns and greater than 0.01 microns. As an example, the filter material is in the form of a filter produced by Millipore (GSWP 01300), the pores of which are 0.22 microns in diameter. The diameter of the aperture 16 in the element 11 is preferably in the range of 50 microns to 300 or 500 microns. In particular, the aperture 16 is of a diameter of 150 microns to 250 microns, for example, 200 microns.

The element 11 is preferably disc shaped or in the form of an elongated tube.

It is preferred that the filter material be saturated with a substance that causes the blood to coagulate. The inventors have found that the hemostatic coagulation of blood platelets is initiated subsequent to trauma of the blood vessels by nucleotides which are liberated very rapidly by the damaged cells. This process can be simulated by saturating the porous material or the filter material with a substance that causes the blood to coagulate, for example, adenosine diphosphate. The solution then passes through the pores of the filter material to the aperture 16 and into the blood that is flowing through the aperture 16.

Once the valves 6 and 8 have been opened, the human blood (for example, a mixture of Na citrate/blood = 1:9), heated to 37 deg. C., for example, is drawn through the capillary 9, the inside diameter of which is 140 microns and the length is 1.6 cm. and the aperture 16. As an example, the negative pressure differential produced by the reservoir and the pump amounts to 5000 Pa. As the blood flows through the aperture 16, this gradually becomes clogged by the blood platelets 12, that build up into a plug. Thus, the flow of blood is gradually slowed down until it finally stops. By selecting the inside diameter of the capillary 9, which can be incorporated ahead of or after the aperture 16, it is possible to provide a precise simulation of the flow resistance of a minor artery, from which the bleeding is taking place. In this manner, it is possible to reproduce hemodynamic behaviour under in vivo conditions.

An example of measurements made with the present system is described below.

Blood from a healthy donor (mean value: SEM Standard Error of the Mean, n=8) is drawn through the aperture. The flow of blood, that is proportional to the viscosity of the blood, amounted to $67+2.8$ $\mu$l/min. after the start of the test. It ended after a bleeding time of $2.9+0.6$ min. with the formation of a clot. During the test, approximately $186+9$ $\mu$l of blood flowed through the aperture 16, which was 150 microns in diameter. Examination of the filter material under an electron microscope revealed the separation of a plug consisting of blood platelets. If the filter material was saturated with an adenosine solution ($10^{-2}$ mol/liter) that hindered the formation of a platelet clot, no clot was formed.

In order to be able to achieve improved reproducibility and shorter bleeding times, the filter material of element 11 can be saturated with an acid-soluble collagen. This provides the advantage that filter fibres which are coated with the collagen promote the adhesion of the blood platelets at the edges of the aperture 16.

It is also possible to cultivate living biological cells on the surface of the porous material or the filter material, respectively, in a culture device, thereby reproducing in vivo conditions more closely.

FIG. 3 shows an especially simple version of the present invention, in which the rise of the blood in a tube 1' is measured; this tube can be arranged either horizontally or vertically, one end of it being connected to a reservoir 2.

At the other end of the tube 1', the element 11 is arranged in a restriction in the tube 1', the base of the restriction forming the base 18'. The capillary 9' is secured beneath the opening of the base 18'. A scale 17' is provided on the tube 1' to make it possible to read off the level of the blood in the tube 1'. It is preferred that this device be configured as a disposable unit and is made of plastic that is assembled tightly, for example, along the line 20, once the element 11 has been installed in the area of the restriction. A device of this kind is suitable chiefly for measuring the quantity of blood that flows in a given time.

For special tests, several apertures rather than just one aperture 16 can be provided in the element 11.

In the versions of the present invention described herein, the blood is drawn by a negative pressure in the reservoir 2, from a container, through the aperture 16 of the element 11. It is also conceivable that the blood can be pressurized from a container that is connected securely to the capillary 9,9' so that it is forced along the capillary 9,9' through the aperture 16.

We claim:

1. A system for measuring bleeding time in vitro, in which the blood can be passed under pressure through a porous element, the system being provided with a system for measurement of the resulting volumetric flow, comprising:

an aperture in said porous element; and a chamber in which said porous element is arranged such that said blood moves substantially through said aperture and substantially no blood moves laterally through said porous element.

2. A system according to claim 1, wherein the diameter of said aperture is no larger than 500 microns.

3. A system according to claim 2, wherein said diameter of said aperture is no larger than 300 microns.

4. A system according to claim 1, wherein said diameter of said aperture is no larger than 50 microns.

5. A system according to claim 1, wherein said diameter of said aperture is between 150 and 250 microns.

6. A system according to claim 1, wherein said porous element consists of filter material that has a pore size that is smaller than 5 microns and greater than 0.01 microns.

7. A system according to claim 1, wherein several apertures are provided in said porous element.

8. A system according to claim 1, wherein a capilliary is incorporated ahead of or after said aperture, and in that the capillary is of an inside diameter that is between 50 and 500 microns.

9. A system according to claim 8, wherein the length of the capillary is 0.5 to 5 cm.

10. A system according to claim 1, wherein said porous element is in the shape of a disc or an elongated tube.

11. A system according to claim 1, wherein said porous element consists of a cellulose-acetate material.

12. A system according to claim 1, wherein said system is configured as a disposable unit and includes a tube that is fitted with a scale, and wherein said tube having at one end a restriction that accommodates the porous element; and a capillary connected to the side opposite said tube in the area of said aperture of the porous element; and said tube, said restriction and said capillary are plastic and are connected tightly and firmly together after said porous element has been inserted into said restriction.

13. A method for measuring bleeding time in vitro in which the blood is passed under pressure through a porous element, the system includes a further system for measurement of the resulting volumetric flow, the method comprises:
providing an aperture is said porous element;
providing a chamber in which said porous element is mounted;
saturating said porous element with a solution that coagulates the blood platelets prior to the start of said test; and,
passing said blood through said aperture of said porous element in such a way that said blood moves substantially through said aperture and no blood moves laterally through said porous element.

14. A method according to claim 13, by using adenosine diphosphate as said solution.

15. A method according to claim 13, by saturating said material of said porous element with collagen.

16. A method according to claim 13, by growing on the surface of said porous element, at least in the area of said aperture, biological, living cells in a culture device, prior to the start of said test.

17. A method according to claim 13, by measuring the displacement of a column of liquid in a tube, that is brought about by a positive or a negative pressure in order to measure the resulting volumetric flow of blood.

18. A method according to claim 13, by measuring the differential of the pressures acting directly on both sides of said aperture to measure the degree to which said aperture is plugged.

* * * * *